United States Patent
Shinzato et al.

(10) Patent No.: US 10,496,794 B2
(45) Date of Patent: Dec. 3, 2019

(54) METHOD OF DETERMINING DOSE OF ERYTHROPOIESIS-STIMULATING AGENT

(71) Applicant: NIPRO CORPORATION, Osaka-Shi (JP)

(72) Inventors: Toru Shinzato, Toyohashi (JP); Yasuyo Maruyama, Toyohashi (JP); Fumihiko Ueno, Tokyo (JP)

(73) Assignee: NIPRO CORPORATION, Osaka-Shi (JP)

( * ) Notice: Subject to any disclaimer, the term of this patent is extended or adjusted under 35 U.S.C. 154(b) by 805 days.

(21) Appl. No.: 14/960,801

(22) Filed: Dec. 7, 2015

(65) Prior Publication Data
US 2016/0085939 A1 Mar. 24, 2016

Related U.S. Application Data

(63) Continuation of application No. PCT/JP2014/065571, filed on Jun. 12, 2014.

(30) Foreign Application Priority Data

Jun. 13, 2013 (JP) ................................ 2013-124676

(51) Int. Cl.
G06F 19/00 (2018.01)
G16H 20/17 (2018.01)
(Continued)

(52) U.S. Cl.
CPC ......... *G06F 19/3456* (2013.01); *G01N 33/72* (2013.01); *G01N 33/721* (2013.01);
(Continued)

(58) Field of Classification Search
None
See application file for complete search history.

(56) References Cited

U.S. PATENT DOCUMENTS 5,951,996 A 9/1999 Zaharia
2003/0198691 A1 10/2003 Cheung et al.
(Continued)

FOREIGN PATENT DOCUMENTS

JP 2003-523940 A 8/2003
JP 2005-247858 A1 9/2005
(Continued)

OTHER PUBLICATIONS

Horowitz et al. Empirical Methods to Calculate an Erythropoiesis-Stimulating Agent Dose Conversion Ratio in Nondialyzed Patients with Chronic Kidney Disease. Journal of Managed Care Pharmacy, vol. 15, No. 9, p. 741-750 (Year: 2009).*
(Continued)

*Primary Examiner* — Olivia M. Wise
(74) *Attorney, Agent, or Firm* — Burr & Brown, PLLC (57) ABSTRACT

A method of determining an ESA dose, which allows a hemoglobin concentration in the blood to be stably maintained at a target value, and which can decrease a range of fluctuation of the hemoglobin concentration with respect to the target value. The method comprises the steps of: setting the target value of the hemoglobin concentration in the blood; calculating a target value of a hemoglobin production rate which allows the hemoglobin concentration to reach the target value; calculating a serum ESA concentration which allows the hemoglobin production rate to reach the target value, from a relationship between the hemoglobin production rate and the ESA concentration; and calculating an amount of administration of an ESA which gives the serum ESA concentration, from a relationship between the ESA concentration and the amount of administration of the ESA, to determine an ESA dose which allows the hemoglobin concentration to reach the target value.

9 Claims, 3 Drawing Sheets

(51) Int. Cl.
*G01N 33/72* (2006.01)
*G16C 20/30* (2019.01)

(52) U.S. Cl.
CPC ....... *G16H 20/17* (2018.01); *G01N 2333/805* (2013.01); *G16C 20/30* (2019.02)

(56) References Cited

U.S. PATENT DOCUMENTS

| | | |
|---|---|---|
| 2004/0157778 A1 | 8/2004 | Cheung et al. |
| 2004/0176297 A1 | 9/2004 | Cheung et al. |
| 2006/0100150 A1 | 5/2006 | Cheung et al. |
| 2006/0128624 A1 | 6/2006 | Cheung et al. |
| 2010/0331362 A1 | 12/2010 | Klaus et al. |
| 2011/0318761 A1 | 12/2011 | Merchant et al. |
| 2013/0052136 A1 | 2/2013 | Chamney et al. |
| 2013/0191097 A1 | 7/2013 | Hocum et al. |

FOREIGN PATENT DOCUMENTS

| | | | | |
|---|---|---|---|---|
| JP | 2008-546644 A | 12/2008 | | |
| JP | 2013-516680 A | 5/2013 | | |
| JP | 2013-527430 A | 6/2013 | | |
| WO | WO-2011082421 A1 * | 7/2011 | ............ | G06F 19/12 |
| WO | 2011/116919 A1 | 9/2011 | | |
| WO | 2013/036836 A2 | 3/2013 | | |

OTHER PUBLICATIONS

Yuzo Watanabe et al., "*Hozonki Mansei Jinzobyo Kanja 0 Taisho to shita Hinketsu Kaizen Koka no Kento—KRN321-SC Shoki Dai II-so Shiken—*", Kidney and Dialysis, Feb. 25, 2010, vol. 68, No. 2, pp. 273-283.

Hirokatsu Atsumi et al., "*Computer 0 Riyo shita Ketsueki Toseki Kanja nl Okeru Tetsu Oyobi Sekkekkyu Zoketsu Shigeki Inshi Seizai no Toyo-ryo Kettei Shien*", Journal of Kanazawa Medical University, Dec. 2011, vol. 36, No. 4, pp. 119-123.

Dana C. Miskulin et al., "*Computerized Decision Support for EPO Dosing in Hemodialysis Patients*," American Journal of Kidney Diseases, Dec. 2009, vol. 54, Issue 6, pp. 1081-1088.

Nobuo Nagano et al., "*Shinsedai Hinketsu Chiryoyaku (KRN321, Darbepoetin Alfa) no Kiso Tokusei*", Kidney and Dialysis, Jun. 25, 2006, vol. 60, No. 6, pp. 1039-1046.

Wei Yang, et al., "*Hemoglobin Variability and Mortality in ESRD*," Journal of American Society of Nephrology, vol. 18 (2007), pp. 3164-3170.

Steven Fishbane, et a., "*Hemoglobin Cycling in Hemodialysis Patients Treated with Recombinant Human Erythropoietin*," International Society of Nephrology, Kidney International, vol. 68 (2005), pp. 1337-1343.

Simon W. Lines, et al., "*A Predictive Algorithm for the Management of Anaemia in Haemodialysis Patients Based on ESA Pharmacodynamics: Better Results for less Work*," Nephrol Dial. Transplant, vol. 27 (2012), pp. 2425-2429.

International Search Report (Application No. PCT/JP2014/065571) dated Aug. 19, 2014.

Japanese Office Action (With English Translation), Japanese Application No. 2013-124676, dated Feb. 28, 2017 (6 pages).

European Search Report, European Application No. 14810587.7, dated Jan. 3, 2017 (6 pages).

\* cited by examiner

METHOD OF DETERMINING DOSE OF ERYTHROPOIESIS-STIMULATING AGENT

CROSS REFERENCE TO RELATED APPLICATION

This application is a continuation of the International Application No. PCT/JP2014/065571 filed on Jun. 12, 2014, which claims the benefit under 35 U.S.C. § 119(a)-(d) of Japanese Application No. 2013-124676 filed on Jun. 13, 2013, the entireties of which are incorporated herein by reference.

BACKGROUND OF THE INVENTION

Field of the Invention

The present invention relates to a method of determining a dose of an erythropoiesis-stimulating agent, and particularly to a method of advantageously determining a dose of an erythropoiesis-stimulating agent, which dose allows a hemoglobin concentration in the blood to be stably maintained at a target value.

Description of Related Art

It is known that in a patient with renal failure suffering from deterioration of the kidney, erythropoietin is not produced or an amount of production of erythropoietin is extremely reduced, resulting in reduction of production of red blood cells, since the production of the red blood cells in the bone marrow is stimulated by erythropoietin mainly produced in the kidney, so that the patient with renal failure suffers from severe anemia, so-called renal anemia.

In order to supply erythropoietin to the patient with renal anemia such as a hemodialysis patient, an erythropoiesis-stimulating agent (ESA) is administered to the patient. The ESA is an erythropoietin preparation prepared by gene recombination, and includes first generation medical agents such as epoetin α and epoetin β (EPO) and a second generation medical agent such as darbepoetin α (DA). The above-indicated medical agents are intravenously administered to the hemodialysis patient through the blood circuit at the time of termination of hemodialysis, for example. At this time, a dose of the ESA is determined based on a doctor's experience such that a hemoglobin concentration in the blood reaches a proper value (10-11 g/dL) set according to guidelines of academic societies. However, the ESA dose determined based on the doctor's experience is sometimes excessively high or excessively low, so that the hemoglobin concentration in the blood inevitably fluctuates over a wide range. It has been difficult to decrease the range of fluctuation of the hemoglobin concentration.

In the case where the hemoglobin concentration in the blood becomes excessively high due to an excessively high ESA dose, there arise not only a problem of an increase in a cost of medical treatment of the patient due to an increase in an amount of use of the costly ESA, but also a problem of an increase in a risk of death of the patient. The problem of an increase in the risk of death also arises where the hemoglobin concentration in the blood becomes excessively low due to an excessively low ESA dose. Further, it is reported that the larger an amount of fluctuation of the hemoglobin concentration in the blood, the higher the risk of death (see Yang W, et al.: J. Am. Soc. Nephrol. 18: 3164-3170, 2007.).

In order to solve the above-described problems caused by the determination of the ESA dose based on the doctor's experience, there was made an algorithm for determining the ESA dose based on a difference between a target value and a present value of the hemoglobin concentration, and a past ESA dose, such that an actually measured value of the hemoglobin concentration will match the target value at the next measurement of the hemoglobin concentration. Namely, according to the algorithm, in the case where the present value of the hemoglobin concentration is lower than the target value, the ESA dose is increased according to the difference therebetween, whereas in the case where the present value of the hemoglobin concentration is higher than the target value, the ESA dose is reduced according the difference therebetween (see Fishbane 5, et al.: Kidney Int. 68: 1337-1343, 2005.). However, the above-described technique still causes fluctuation of the actually measured value of the hemoglobin concentration over a wide range, excessively above or excessively below the target value, so that it has been difficult to decrease the range of fluctuation.

Further, there is reported a method of determining the ESA dose, which is employed where the hemoglobin concentration is measured once per month. In this method, the hemoglobin concentration to be achieved one month later is estimated from the hemoglobin concentrations respectively measured one month ago and at the present moment, and in the case where the hemoglobin concentration estimated to be achieved one month later is lower than the target value of the hemoglobin concentration, the ESA dose is increased according to a difference therebetween, whereas in the case where the hemoglobin concentration estimated to be achieved one month later is higher than the target value, the ESA dose is reduced according to a difference therebetween (see Lines S W, et al.: Nephrol. Dial. Transplant. 27: 2425-2429, 2012.). However, according to the above-described method of determination of the ESA dose so as to decrease the difference between the hemoglobin concentration estimated to be achieved one month later and the target value, it has been impossible to sufficiently decrease the range of fluctuation of the actually measured value of the hemoglobin concentration above or below the target value.

SUMMARY OF THE INVENTION

The present invention was made in view of the background art described above. It is an object of the invention to provide a method of determining an ESA dose, which allows the hemoglobin concentration in the blood to be stably maintained at a target value, and which can decrease the range of fluctuation of the hemoglobin concentration in the blood.

To achieve the above-described object, the present invention can be preferably embodied in various preferred modes which will be described below. The preferred modes of the invention described below may be practiced in any combination. It is to be understood that the preferred modes and technical features of the present invention are not limited to those described below, and can be recognized based on the inventive concept disclosed in the whole specification and the drawings.

(1) A method of determining a dose of an ESA, comprising: a first step of setting a target value of a hemoglobin concentration in blood; a second step of calculating a target value of a hemoglobin production rate which allows the hemoglobin concentration to reach the above-described target value; a third step of calculating a concentration of an ESA, which concentration allows the hemoglobin production rate to reach the above-described target value, from a relationship between the hemoglobin production rate at a present moment and the concentration of the ESA up to the present moment; and a fourth step of calculating an amount of administration of the ESA, which amount gives the above-described concentration of the ESA, from a relationship between the concentration of the ESA and its amount of administration, to determine a dose of the ESA, which dose allows the hemoglobin concentration to reach the above-described target value.

(2) The method of determining the dose of the ESA according to the above-described mode (1), wherein the above-described target value of the hemoglobin production rate is obtained by dividing a target total amount of hemoglobin by an average lifespan of red blood cells.

(3) The method of determining the dose of the ESA according to the above-described mode (1) or (2), wherein the concentration of the ESA is calculated in the above-described third step by using a relational expression representing that the hemoglobin production rate is proportional to a logarithmic value of the concentration of the ESA.

(4) The method of determining the dose of the ESA according to the above-described mode (1) or (2), wherein the concentration of the ESA is calculated in the above-described third step by using a relational expression representing that the hemoglobin production rate is linearly proportional to the concentration of the ESA.

(5) The method of determining the dose of the ESA according to any one of the above-described modes (1) to (4), wherein the above-described third step comprises the steps of: obtaining the hemoglobin production rate at a present measurement of the hemoglobin concentration; calculating a mean concentration of the ESA in a length of time between a last measurement and the present measurement of the hemoglobin concentration, from an amount of the ESA administered between the last and present measurements of the hemoglobin concentration; calculating a value a indicating a degree of sensitivity of hemoglobin production with respect to the concentration of the ESA, from the above-described mean concentration of the ESA and the above-described hemoglobin production rate; and calculating a mean concentration of the ESA, which mean concentration allows the hemoglobin concentration to reach the above-described target value, from the above-described value a and the above-described target value of the hemoglobin production rate.

(6) The method of determining the dose of the ESA according to the above-described mode (5), wherein the above-described dose of the ESA in the above-described fourth step, which dose allows the hemoglobin concentration to reach the above-described target value, is determined from the above-described mean concentration of the ESA, which mean concentration allows the hemoglobin concentration to reach the above-described target value.

As described above, in the present invention, the hemoglobin production rate which allows the hemoglobin concentration to reach the target value, in other words, the target value of the hemoglobin production rate is calculated from the target value of the hemoglobin concentration, and then, the serum ESA concentration which allows the hemoglobin production rate to reach the above-described target value is calculated, and thereafter, the ESA dose which gives the above-described serum ESA concentration is calculated. By administering the ESA by the amount calculated as described above, the hemoglobin concentration in the blood reaches the target value with a high degree of stability within a red-blood-cell's lifespan of about 90 days. Moreover, the serum ESA concentration which allows the hemoglobin production rate to reach the target value is calculated based on the relationship between the hemoglobin production rate at the present measurement of the hemoglobin concentration and the mean ESA concentration in a length of time between the last and present measurements of the hemoglobin concentration, so that it is possible to obtain an accurate value of the serum ESA concentration which allows the hemoglobin production rate to reach the target value.

DETAILED DESCRIPTION OF THE INVENTION

By the way, a lifespan of a red blood cell which carries hemoglobin is considered to be about 90 days in a hemodialysis patient, while an interval of measurement of a hemoglobin concentration is set at about one month (four or five weeks). Accordingly, hemoglobin existing in the blood is wholly replaced with new one while the hemoglobin concentration is measured three times. Accordingly, in the case where a rate of production of hemoglobin is constant, the hemoglobin concentration is stabilized at a value corresponding to the hemoglobin production rate, within about 90 days. Therefore, in the present invention, an ESA concentration which can give the hemoglobin production rate that allows the hemoglobin concentration to reach a target value within 90 days is calculated, and an ESA dose which can give the above-indicated ESA concentration is calculated.

Provided that a state in which a constant amount (Gg/day) of hemoglobin is produced every day and hemoglobin is removed every day by the same amount as produced is defined as a stable state of hemoglobin dynamics, the hemoglobin production rate in the above-described stable state is obtained by dividing a product of the hemoglobin concentration and a volume of distribution of hemoglobin (blood volume), which product represents a total amount of hemoglobin in the human body, by a lifespan of hemoglobin, namely, the number of days between the production and removal of hemoglobin, as described below in more detail. In this respect, it is noted that the lifespan of hemoglobin is equal to that of the red blood cell which carries hemoglobin, so that the lifespan of hemoglobin is hereinafter referred to as a red-blood-cell lifespan.

Assuming that the stable state of the hemoglobin dynamics lasts for at least TR days which represent a period of survival of the red blood cells, the oldest hemoglobin existing in the blood at a given point of time is produced TR days ago. This means that hemoglobin existing in the blood at the given point of time is wholly produced within the past TR days. Therefore, in the stable state of the hemoglobin dynamics, the total amount (totalHg) of hemoglobin existing in the blood at the given point of time can be represented by the following formula (1).

$$totalHg = TR \times G \tag{1}$$

On the other hand, the hemoglobin concentration (CHg) in the blood is obtained by dividing the above-indicated total amount of hemoglobin by the blood volume (BV) which is estimated to be 8% of the body weight (in the case of a man) or 7% of the body weight (in the case of a woman), and can be represented by the following formula (2).

$$CHg = totalHg/BV \tag{2}$$

By applying the above-indicated formula (1) to the formula (2), the following formula (3a) can be obtained.

$$CHg = TR \times G/BV \tag{3a}$$

Further, the formula (3a) can be converted into the following formula (3b).

$$G = CHg \times BV/TR \tag{3b}$$

In the case where an amount of removal of hemoglobin is larger or smaller than an amount of its production, namely, where the hemoglobin dynamics is in an unstable state, the hemoglobin concentration decreases or increases. At this time, the decrease or increase in the hemoglobin concentration generally results from a decrease or increase in the amount of production of hemoglobin, rather than an increase or decrease in the amount of removal of hemoglobin.

Accordingly, provided that the amount of production of hemoglobin per day is defined as the hemoglobin production rate, in the case where the hemoglobin dynamics is in the unstable state and the hemoglobin concentration is fluctuated, it can be said that a difference between total amounts of hemoglobin in the human body at respective two points of time is generated by accumulation of a difference between the hemoglobin production rates at those two points of time. Therefore, the difference between the hemoglobin production rates at the respective two points of time can be obtained by dividing the difference between the total amounts of hemoglobin at those two points of time by the number of days between those two points of time. This relationship is represented by a formula (4) given below. In this respect, it is noted that in the formula (4), $\Delta G$ denotes the difference between the hemoglobin production rates at the respective two points of time, CHg 1 denotes the hemoglobin concentration at a given point of time, CHg 2 denotes the hemoglobin concentration measured before the above-indicated given point of time, BV denotes the blood volume, and TT denotes the number of days between the above-indicated two points of time.

$$\Delta G = (CHg1 \times BV - CHg2 \times BV)/TT \tag{4}$$

When the hemoglobin production rate is increasing, $\Delta G$ in the formula (4) is larger than 0 ($\Delta G > 0$). On the other hand, when the hemoglobin production rate is decreasing, $\Delta G$ in the formula (4) is smaller than 0 ($\Delta G < 0$). In other words, in the case where the hemoglobin concentrations at respective two points of time are different from each other (in the case where the hemoglobin dynamics is in the unstable state), the hemoglobin production rate is increased by an amount represented by $\Delta G$, as compared with the hemoglobin production rate in the case where the hemoglobin concentrations at the respective two points of time are equal to each other (in the case where the hemoglobin dynamics is in the stable state). Accordingly, the hemoglobin production rate (Greal) in the unstable state is obtained by adding $\Delta G$ to G obtained according to the above-indicated formula (3b), and represented by the following formula (5a).

$$Greal = G + \Delta G \tag{5a}$$

By applying the above-indicated formulas (3b) and (4) to the formula (5a), a formula (5b) for obtaining the hemoglobin production rate in the unstable state is obtained as indicated below. In order to clarify a reference point of time, in the formula (5b), the hemoglobin concentration indicated in the formula (3b) is converted into CHg 2. Further, in the formula (5b), TR denotes the red-blood-cell lifespan, while TT denotes the number of days between the two points of time.

$$Greal = CHg2 \times BV/TR + (CHg1 \times BV - CHg2 \times BV)/TT \tag{5b}$$

Figure 1:
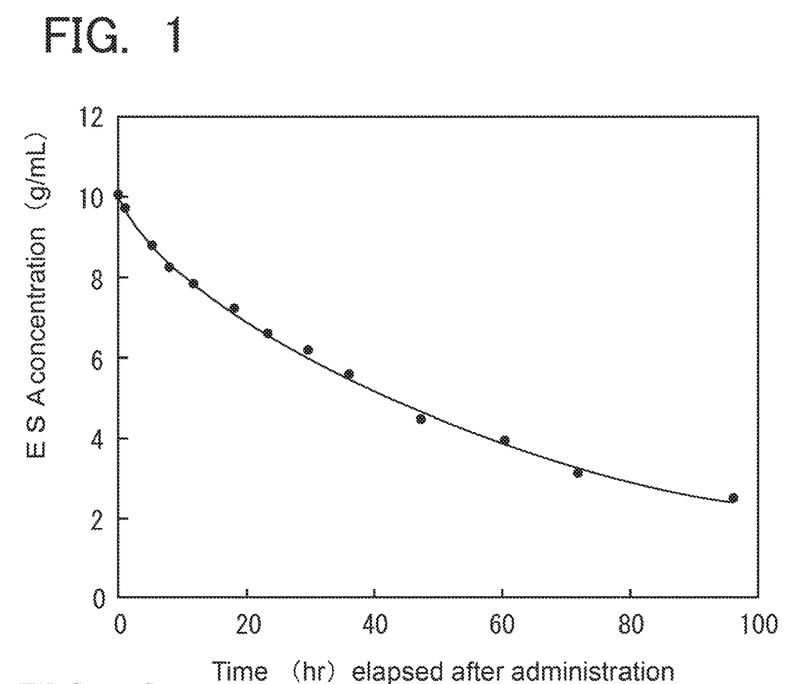
FIG. 1 is a graph showing an example of a relationship between a concentration of an ESA administered to the human body and a time which has passed after administration of the ESA.

On the other hand, it is recognized that a serum ESA concentration generated as a result of administration of the ESA to the human body decreases exponentially, as shown in FIG. 1. Namely, an attenuation curve of the ESA concentration is represented by a formula (6) given below. In the formula (6), b is a constant, and t denotes a period of time which has passed after the administration of the ESA. Further, $C_{ESA}$, (t) denotes the ESA concentration at a point of time at which the above-indicated period t has passed after the administration of the ESA, while $C_{ESA}$ (0) denotes the ESA concentration right after the administration of the ESA, namely, at a point of time at which the above-indicated period t is zero.

$$C_{ESA}(t) = C_{ESA}(0) \times \exp(-b \times t) \tag{6}$$

In this respect, it is noted that $C_{ESA}$ (0)=$D_{ESA}/V_{ESA}$, wherein $D_{ESA}$, denotes the ESA dose, and $V_{ESA}$ denotes the volume of distribution of the ESA. As the constant b, there is used a value obtained based on already reported data, depending on the kind of the ESA. For instance, in the case of darbepoetin α, b=0.40943, while in the case of epoetin α and epoetin β, b=1.2053.

As for the frequency of administration of the ESA, epoetin α and epoetin β are generally administered 3 times per week, 12-15 times per month, and every 2 or 3 days, while darbepoetin β is generally administered once per week, 4-5 times per month, and every 7 days. Where the above-indicated kinds of ESA are administered at the respective frequencies described above, the serum ESA concentration generated as a result of the previous administration of the ESA decreases to almost zero at the time of the ESA administration at a given point of time. Accordingly, provided that the ESA is administered n times between the last measurement of the hemoglobin concentration and the present measurement of the hemoglobin concentration, a mean ESA concentration ($MC_{ESA}$) as an integral average value of the ESA concentration in a length of time between the last and present measurements of the hemoglobin concentration is calculated according to the following formula (7a) or (7b).

$$MC_{ESA} = [C_{ESA}1(0)\int_0^{TD}\exp(-b \times t)dt + C_{ESA}2(0)\int_0^{TD}\exp(-b \times t)dt + \ldots + C_{ESA}n(0)\int_0^{TD}\exp(-b \times t)dt]/TT \tag{7a}$$

$$MC_{ESA} = [C_{ESA}1(0) + C_{ESA}2(0) + \ldots + C_{ESA}n(0)]/TT \times \int_0^{TD}\exp(-b \times t)dt \tag{7b}$$

Figure 2:
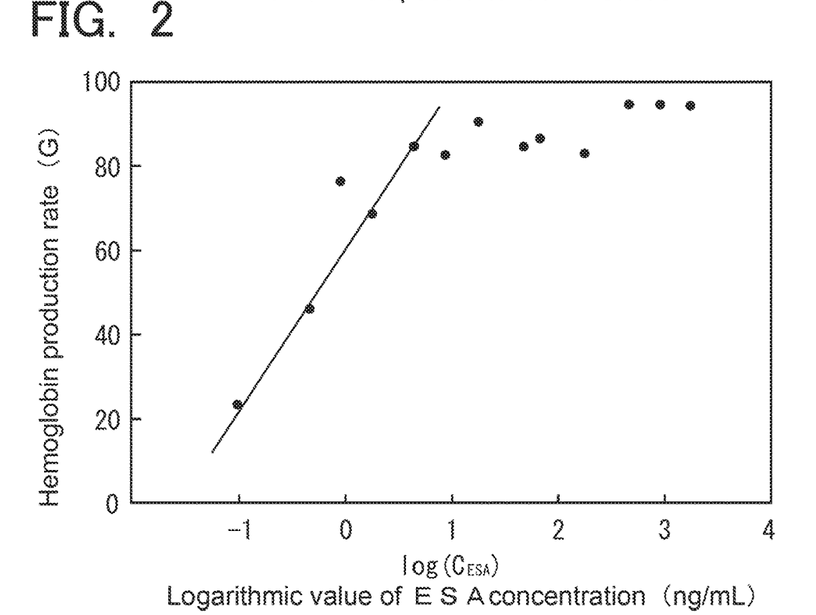
FIG. 2 is a graph showing an example of a relationship between a hemoglobin production rate and a logarithmic value: log $(C_{ESA})$ of the ESA concentration.

In the formulas (7a) and (7b), the FIGS. 1,2, . . . n) following $C_{ESA}$ denote order of the ESA administration, while TD denotes an interval of the ESA administration. On the other hand, $C_{ESA}$ (0)=$D_{ESA}/V_{ESA}$, wherein $D_{ESA}$ denotes the ESA dose, and $V_{ESA}$ denotes the volume of distribution of the ESA. By applying this equation to the above-indicated formula (7b), the following formula (8a) can be obtained.

$$MC_{ESA}=[D_{ESA}1D_{ESA}2+\ldots+D_{ESA}n]/V_{ESA}/TT\times\int_0^{TD}\exp(-b\times t)dt \quad (8a)$$

In the formula (8a), the FIGS. 1,2, . . . n) following $D_{ESA}$ denote the order of the ESA administration. Further, $V_{ESA}$ denoting the volume of distribution of the ESA is represented by about 5% of the body weight, specifically, 5.2% of the body weight in the case of a man, and 4.6% of the body weight in the case of a woman. The above-indicated formula (8a) can be converted into the following formula (8b).

$$MC_{ESA}=[D_{ESA}1+D_{ESA}2+\ldots+D_{ESA}n]\times[1-\exp(-b\times TD)]/b/V_{ESA}/TT \quad (8b)$$

By the way, according to an in vitro experiment, the hemoglobin production rate (G) in a solution in which the red blood cells are being cultured is proportional to a logarithmic value of the ESA concentration ($C_{ESA}$) [see Noburo Nagano et al., KIDNEY AND HEMODIALYSIS, 60(6), 1039-1046, 2006] as shown in FIG. 2, for example, and can be represented by a formula (9) given below. In the formula (9), a is a constant and recognized as a value indicating a degree of sensitivity of the hemoglobin production with respect to the ESA concentration.

$$G=a\times ln(C_{ESA}) \quad (9)$$

In the formula (9), when the ESA concentration decreases close to zero, the logarithmic value of the ESA concentration decreases toward minus infinity, and accordingly, G decreases toward the minus infinity. Therefore, the formula (9) has a disadvantage that it is not effective where the ESA concentration is extremely low.

However, the above-described relationship between the hemoglobin production rate and the ESA concentration can be approximated to a linearly proportional relationship where the serum ESA concentration of a patient is within a normal range. Where the relationship between the hemoglobin production rate and the serum ESA concentration is approximated to the linearly proportional relationship, some error is generated in a calculated value of G, within the normal range of the serum ESA concentration. However, the above-described approximation has an advantage that it is effective even where the ESA concentration is low.

The above-indicated formula (9) is also applicable to the hemoglobin production rate within the human body. Therefore, by applying the above-described mean ESA concentration to the formula (9), the following formula (10a) can be obtained.

$$G=a\times ln(MC_{ESA}) \quad (10a)$$

Further, by converting the formula (10a), a formula (10b) for giving a as the value indicating the degree of sensitivity of the hemoglobin production with respect to the ESA concentration can be obtained, as indicated below.

$$a=G/ln(MC_{ESA}) \quad (10b)$$

It is noted that the value a in the formula (10b) changes among different patients and depending on the state of the patients, so that the value a is calculated every time of measurement of the hemoglobin concentration, from the present value of measurement of the hemoglobin concentration, the last value of measurement of the hemoglobin concentration, and the mean ESA concentration in a length of time between the last and present measurements of the hemoglobin concentration.

By the way, the hemoglobin concentration of a hemodialysis patient is measured at a frequency of about every month (every 4 or 5 weeks) at the time of initiation of hemodialysis. In the present invention, the ESA dose which allows the hemoglobin production rate to reach a target value at the next time of blood sampling is determined based on the present value of measurement of the hemoglobin concentration, the last value of measurement of the hemoglobin concentration (value measured one month ago), and an amount of the ESA administered to the patient within the one month between the last and present measurements, and the ESA is administered to the patient by the thus determined dose. The ESA dose which allows the hemoglobin production rate to reach the target value at the next time of blood sampling is determined by a method described below.

In a state in which the hemoglobin concentration is stably maintained at the target value, hemoglobin existing in the blood is wholly produced within the past 90 days at a constant rate, and accumulated in the blood. Accordingly, the target value of the hemoglobin production rate is obtained by dividing a target total amount of hemoglobin as a product of the target value of the hemoglobin concentration and the blood volume, by 90 days as the average lifespan of the red blood cells. Namely, the target value of the hemoglobin production rate is represented by a formula (11) given below, provided that target CHg denotes the target value of the hemoglobin concentration representing an amount of hemoglobin desired to exist within the human body at the next time of blood sampling, BV denotes the blood volume, and TR denotes the average red-blood-cell lifespan (90 days).

$$\text{target}G=\text{target}CHg\times BV/TR \quad (11)$$

On the other hand, provided that the mean ESA concentration which allows the hemoglobin concentration to reach the target value is represented by target $MC_{ESA}$, a formula (12) given below is obtained by applying target $MC_{ESA}$ and target G to the above-indicated formula (10a).

$$\text{target}G=a\times ln(\text{target}MC_{ESA}) \quad (12a)$$

By converting the formula (12a), a formula (12b) for calculating the mean ESA concentration allowing the hemoglobin concentration to reach the target value, from the target value of the hemoglobin concentration, is obtained as indicated below.

$$\text{target}MC_{ESA}=\exp(\text{target}G/a) \quad (12b)$$

In this respect, it is noted that the value a is calculated according to the above-indicated formula (10b) by using the hemoglobin production rate at the present moment and the mean ESA concentration based on the previous ESA administrations.

Then, by applying the above-indicated formula (11) to the formula (12b), a formula (13) for obtaining the mean ESA concentration allowing the hemoglobin concentration to reach the target value, from the target value of the hemoglobin concentration, is obtained as indicated below.

$$\text{target}MC_{ESA}=\exp(\text{target}CHg\times BV/TR/a) \quad (13)$$

After the mean ESA concentration which allows the hemoglobin concentration to reach the target value is calculated according to the formula (13), the ESA dose which gives the above-described mean ESA concentration is obtained. Initially, by applying, to the above-indicated formula (8b), a total amount of the ESA (target $D_{ESA}1$+target $D_{ESA}2$+ . . . +target $D_{ESA}n$) to be administered from the present moment to a target point of time in order to achieve the mean ESA concentration (target $MC_{ESA}$) which allows the hemoglobin concentration to reach the target value, a formula (14a) indicating a relationship between target $MC_{ESA}$ and target $D_{ESA}$ 1, target $D_{ESA}$ 2, . . . target $D_{ESA}$ n is obtained as indicated below.

$$\text{target}MC_{ESA} = \{\text{target}D_{ESA}1 + \text{target}D_{ESA}2 + \ldots + \text{target}D_{ESA}n\} \times \{1 - \exp(-b \times TD)\}/b/V_{ESA}/TT \quad (14a)$$

By converting the formula (14a), a formula (14b) for obtaining the total amount of administration of the ESA (target $D_{ESA}$ 1+target $D_{ESA}$ 2+ . . . +target $D_{ESA}$ n) allowing the hemoglobin concentration to reach the target value, from target $MC_{ESA}$, is obtained as indicated below.

$$\text{target}D_{ESA}1 + \text{target}D_{ESA}2 + \ldots + \text{target}D_{ESA}n = \text{target}MC_{ESA} \times b \times V_{ESA} \times TT/\{1 - \exp(-b \times TD)\} \quad (14b)$$

By the way, where the amount of administration of the ESA which allows the hemoglobin concentration to reach the target value is calculated according to the formula (14b), the calculated value indicates a total amount of the ESA doses (target $D_{ESA}$ 1, target $D_{ESA}$ 2, . . . target $D_{ESA}$ n) to be administered from the present point of time of measurement to the target point of time of measurement, and does not indicate each of those ESA doses. Therefore, in the case where the ESA is to be administered to the patient by the amount calculated according to the formula (14b), the dose per administration should be determined by dividing the amount calculated according to the formula (14b) by a required number of administration, since the amount calculated according to the formula (14b) is the total amount of the ESA doses to be administered from the present point of time of measurement to the target point of time of measurement. On the other hand, the ESA is marketed while being accommodated in ampoules, so that the ESA is administered to the patient on an ampoule-to-ampoule basis. For instance, epoetin α and epoetin Δ are marketed while being accommodated in the ampoules respectively containing 750 units, 1500 units and 3000 units of epoetin α or epoetin β, while darbepoetin α is marketed while being accommodated in the ampoules respectively containing 10 μg, 15 μg, 20 μg, 30 μg, 40 μg and 60 μg of darbepoetin α. The amount of the ESA accommodated in each ampoule does not necessarily match the theoretical ESA dose per administration obtained by dividing, by the required number of administration, the total amount of the ESA doses to be administered from the present point of time of measurement to the target point of time of measurement, which total amount of the ESA doses is obtained according to the above-indicated formula (14b).

Therefore, in practice, the ESA is administered by using the ampoule containing the ESA in an amount closest to the above-described theoretical ESA dose per administration obtained by dividing, by the required number of administration, the total amount of the ESA doses to be administered from the present point of time of measurement to the target point of time of measurement, which total amount of the ESA doses is obtained according to the above-indicated formula (14b).

Figure 3:
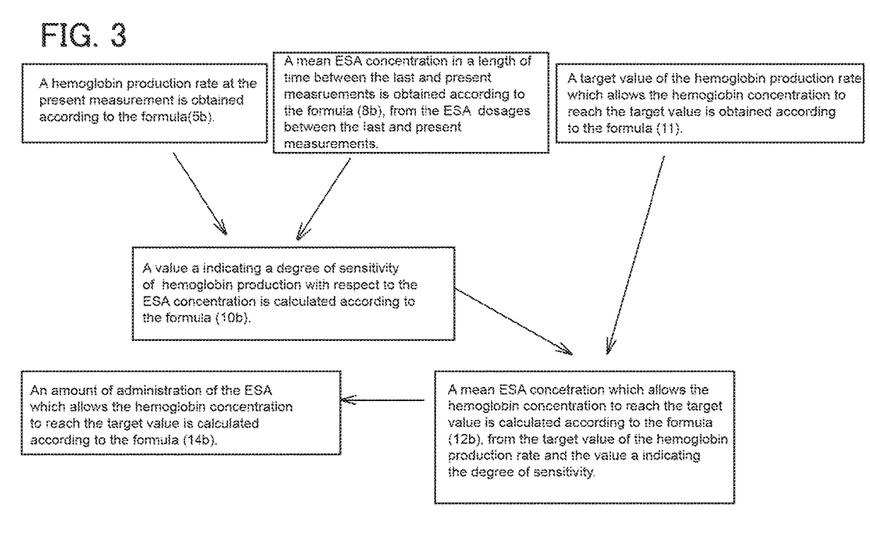
FIG. 3 is a flowchart showing a specific example of a method of determining an ESA dose according to the invention.

The above-described specific steps of the method of determining the ESA dose according to the invention are shown in the flowchart of FIG. 3. Namely, in the method of the invention, the target value of the hemoglobin concentration in the blood is initially determined for each patient, within a range of 10-11 g/dL, which range is considered to be the proper range according to the guidelines. Then, the target value of the hemoglobin production rate which allows the hemoglobin concentration to reach the above-indicated target value, for example, the target value of 10.5 g/dL, is obtained according to the above-indicated formula (11). On the other hand, the hemoglobin production rate at the present measurement of the hemoglobin concentration is obtained according to the above-indicated formula (5b), and the mean ESA concentration in a length of time between the last and present measurements of the hemoglobin concentration is calculated according to the above-indicated formula (8b), from the amount of the ESA administered between the last and present measurements. Then, the value a indicating the degree of sensitivity of the hemoglobin production rate with respect to the mean ESA concentration is calculated according to the above-indicated formula (10b). The mean ESA concentration which allows the hemoglobin concentration to reach the target value is calculated according to the above-indicated formula (12b), from the above-indicated value a and the target value of the hemoglobin production rate. Thereafter, the amount of the ESA to be administered from the present point of time of measurement to the target point of time of measurement in order to allow the hemoglobin concentration to reach the target value is calculated according to the above-indicated formula (14b), from the mean ESA concentration which allows the hemoglobin concentration to reach the target value.

By administering, to the patient, the ESA such as epoetin α, epoetin β and darbepoetin α by an amount calculated by the method of determining the ESA dose according to the invention, the target value of the hemoglobin concentration can be achieved with a high degree of stability within the red-blood-cell lifespan of about 90 days, to advantageously improve a degree of anemia of the patient and remove factors which cause an increase in the risk of death.

EXAMPLE

To clarify characteristics of the invention more specifically, a representative example of the invention will be described. However, it goes without saying that the invention is by no means limited to the details of the illustrated example.

Initially, an ESA (darbepoetin α) was administered to a male patient of 66 years old (body weight: 53.2 kg) for six months, by employing a method of controlling an ESA dose according to a conventional algorithm, and setting the target value of the hemoglobin concentration at 10.5 g/dL. In this respect, it is noted that a relationship between the hemoglobin concentration (Hg) and the ESA dose according to the conventional algorithm is indicated below.

| Hemoglobin concentration (Hg) | ESA dose |
| --- | --- |
| Hg >13.0 g/dL | resumed after interruption of two weeks |
| 13.0 g/dL ≥ Hg > 12.0 g/dL | reduced by 25-50% |
| 12.0 g/dL ≥ Hg > 11.0 g/dL | reduced by 25% |
| 11.0 g/dL ≥ Hg > 10.0 g/dL | unchanged |
| 10.0 g/dL ≥ Hg | increased by 25-50% |

Then in the subsequent six months, the ESA (darbepoetin α) was administered to the patient by determining the ESA dose according to the method of the invention, and setting the target value of the hemoglobin concentration at 10.5 g/dL.

Figure 4:
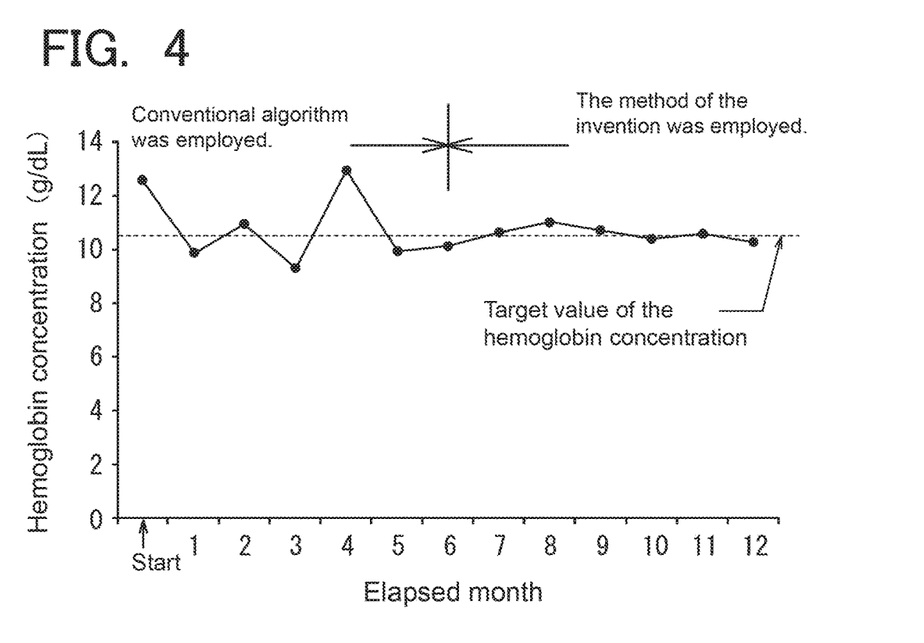
FIG. 4 is a graph showing a change with a passage of time of a hemoglobin concentration in the blood measured in an Example wherein the ESA was administered according to a conventional algorithm for six months, and then administered according to the method of the invention for six months.
Figure 5:
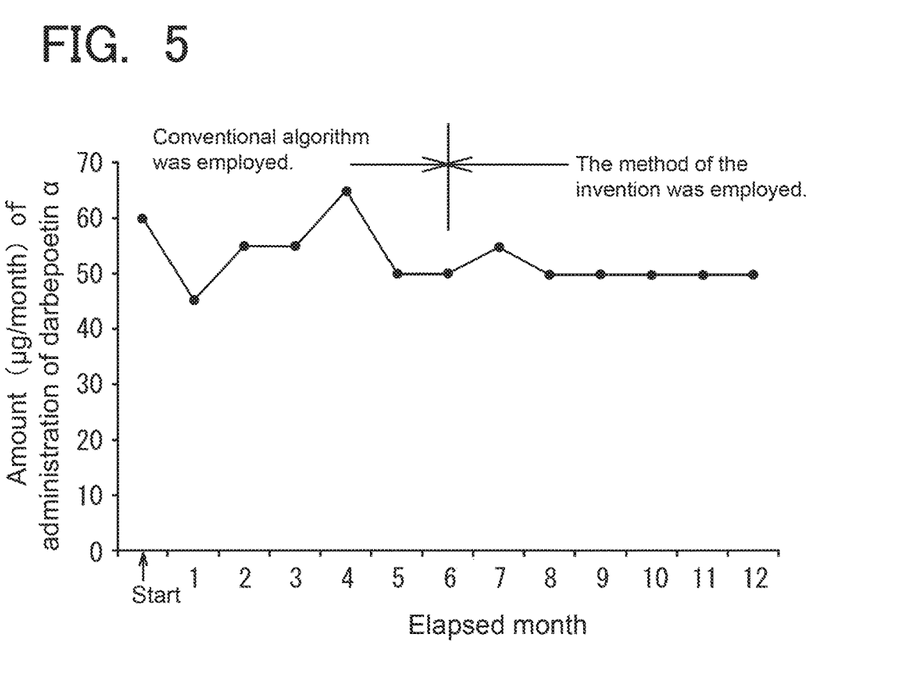
FIG. 5 is a graph showing a change of an amount (μg/month) of administration of darbepoetin α in each month in the Example wherein the ESA dose was controlled according to the conventional algorithm for six months, and then controlled according to the method of the invention for six months.

A change of the hemoglobin concentration (g/dL) of the patient measured every month at the time of blood sampling is shown in FIG. 4, and a change of an amount (μg/month) of administration of darbepoetin determined based on measured values of the hemoglobin concentration is shown in FIG. 5, together with the number of elapsed months.

As is apparent from FIGS. 4 and 5, an average value of the hemoglobin concentration is 10.9 g/dL in the case where the ESA (darbepoetin α) dose was controlled by the conventional algorithm, while the average value of the hemoglobin concentration is 10.7 g/dL in the case where the ESA dose was controlled by the method of the present invention, so that there is almost no difference between the above-indicated average values. On the other hand, a standard deviation (SD) and a coefficient of fluctuation (CV) of the hemoglobin concentration are respectively 1.31 g/dL and 0.12 in the case where the ESA (darbepoetin α) dose was controlled by the conventional algorithm, while the standard deviation and the coefficient of fluctuation of the hemoglobin concentration are respectively 0.22 g/dL and 0.02 in the case where the ESA dose was controlled by the method of the present invention. This means that where the method of the invention was employed, the hemoglobin concentration fluctuates only by a small amount. Where the hemoglobin concentration fluctuates by a large amount as in the case where the conventional algorithm was employed, a risk of death increases.

In the case where the conventional algorithm was employed, an amount of use of the ESA (darbepoetin α) was 54±6.2 μg/month, whereas in the case where the method of the invention was employed, the amount of use of the ESA was 51±1.9 μg/month. This reveals that the amount of use of the ESA can be reduced according to the method of the invention, as compared with that required according to the conventional algorithm.

The invention claimed is:

1. A method of treating a patient, comprising:
   a first step of setting a target value of a hemoglobin concentration in blood;
   a second step of calculating a target value of a hemoglobin production rate which allows the hemoglobin concentration to reach said target value;
   a third step of calculating a calculated concentration of an erythropoiesis-stimulating agent, which calculated concentration allows the hemoglobin production rate to reach said target value, from a relationship between the hemoglobin production rate at a present moment and the concentration of the erythropoiesis-stimulating agent up to the present moment;
   a fourth step of calculating an amount of administration of the erythropoiesis-stimulating agent, which amount gives said calculated concentration of the erythropoiesis-stimulating agent, from a relationship between the concentration of the erythropoiesis-stimulating agent and its amount of administration, to determine a dose of the erythropoiesis-stimulating agent, which dose allows the hemoglobin concentration to reach said target value; and
   a fifth step of administering to said patient said dose of the erythropoiesis-stimulating agent;
   said third step comprising the steps of:
      obtaining the hemoglobin production rate at a present measurement of the hemoglobin concentration;
      calculating a mean concentration of the erythropoiesis-stimulating agent in a length of time between a last measurement and the present measurement of the hemoglobin concentration, from an amount of the erythropoiesis-stimulating agent administered between the last and present measurements of the hemoglobin concentration;
      calculating a value a indicating a degree of sensitivity of hemoglobin production with respect to the concentration of the erythropoiesis-stimulating agent, from said mean concentration of the erythropoiesis-stimulating agent and said hemoglobin production rate; and
      calculating said calculated concentration of the erythropoiesis-stimulating agent from said value a and said target value of the hemoglobin production rate.

2. The method of determining the dose of the erythropoiesis-stimulating agent according to claim 1, wherein said target value of the hemoglobin production rate is obtained by dividing a target total amount of hemoglobin by an average lifespan of red blood cells.

3. The method of treating a patient according to claim 1, wherein:
   the concentration of the erythropoiesis-stimulating agent is calculated in said third step by using a relational expression representing that the hemoglobin production rate is proportional to a logarithmic value of the concentration of the erythropoiesis-stimulating agent.

4. The method of determining the dose of the erythropoiesis-stimulating agent according to claim 1, wherein the concentration of the erythropoiesis-stimulating agent is calculated in said third step by using a relational expression representing that the hemoglobin production rate is linearly proportional to the concentration of the erythropoiesis-stimulating agent.

5. The method of determining the dose of the erythropoiesis-stimulating agent according to claim 1, wherein the hemoglobin production rate at the present measurement of the hemoglobin concentration is obtained according to the following formula (5b):

$$Greal = CHg2 \times BV/TR + (CHg1 \times BV - CHg2 \times BV)/TT \tag{5b}$$

wherein Greal denotes the hemoglobin production rate in an unstable state, CHg 1 denotes the hemoglobin concentration at a given point of time, CHg 2 denotes the hemoglobin concentration measured before the given point of time, BV denotes a blood volume, TR denotes an average red-blood-cell lifespan and TT denotes the number of days between the two points of time.

6. A method of treating a patient, comprising:
   a first step of setting a target value of a hemoglobin concentration in blood;
   a second step of calculating a target value of a hemoglobin production rate which allows the hemoglobin concentration to reach said target value;
   a third step of calculating a concentration of an erythropoiesis-stimulating agent, which concentration allows the hemoglobin production rate to reach said target value, from a relationship between the hemoglobin production rate at a present moment and the concentration of the erythropoiesis-stimulating agent up to the present moment;
   a fourth step of calculating an amount of administration of the erythropoiesis-stimulating agent, which amount gives said concentration of the erythropoiesis-stimulating agent, from a relationship between the concentration of the erythropoiesis-stimulating agent and its amount of administration, to determine a dose of the erythropoiesis-stimulating agent, which dose allows the hemoglobin concentration to reach said target value; and
   a fifth step of administering to said patient said dose of the erythropoiesis-stimulating agent;
   said third step comprising calculating said concentration of an erythropoiesis-stimulating agent according to the following formula (12b):

$$\text{target } MC_{ESA} = \exp(\text{target } G/a) \tag{12b}$$

wherein target $MC_{ESA}$ denotes a mean concentration of the erythropoiesis-stimulating agent which allows the hemoglobin concentration to reach said target value, target G denotes said target value of the hemoglobin production rate, and a denotes a value indicating a degree of sensitivity of the hemoglobin production with respect to the concentration of the erythropoiesis-stimulating agent.

7. The method of determining the dose of the erythropoiesis-stimulating agent according to claim 1, wherein the value a indicating a degree of sensitivity of hemoglobin production with respect to the concentration of the erythropoiesis-stimulating agent is calculated from said mean concentration of the erythropoiesis-stimulating agent and said hemoglobin production rate according to the following formula (10b):

$$a = G/\ln(MC_{ESA}) \tag{10b}$$

wherein G is the hemoglobin production rate and $MC_{ESA}$ denotes said mean concentration of the erythropoiesis-stimulating agent.

8. A method of treating a patient, comprising:
 a first step of setting a target value of a hemoglobin concentration in blood;
 a second step of calculating a target value of a hemoglobin production rate which allows the hemoglobin concentration to reach said target value;
 a third step of calculating a concentration of an erythropoiesis-stimulating agent, which concentration allows the hemoglobin production rate to reach said target value, from a relationship between the hemoglobin production rate at a present moment and the concentration of the erythropoiesis-stimulating agent up to the present moment;
 a fourth step of calculating an amount of administration of the erythropoiesis-stimulating agent, which amount gives said concentration of the erythropoiesis-stimulating agent, from a relationship between the concentration of the erythropoiesis-stimulating agent and its amount of administration, to determine a dose of the erythropoiesis-stimulating agent, which dose allows the hemoglobin concentration to reach said target value; and
 a fifth step of administering to said patient said dose of the erythropoiesis-stimulating agent;
 said second step comprising calculating said target value of a hemoglobin production rate according to the following formula (11):

$$\text{target } G = \text{target } CHg \times BV/TR \tag{11}$$

wherein target G denotes said target value of the hemoglobin production rate, target CHg denotes said target value of the hemoglobin concentration, BV denotes a blood volume and TR denotes an average red-blood-cell lifespan.

9. The method of determining the dose of the erythropoiesis-stimulating agent according to claim 1, wherein said mean concentration of the erythropoiesis-stimulating agent in a length of time between the last measurement and the present measurement of the hemoglobin concentration is calculated from the amount of the erythropoiesis-stimulating agent administered between the last and present measurements of the hemoglobin concentration according to the following formula (8b):

$$MC_{ESA} = [D_{ESA}1 + D_{ESA}2 + \ldots + D_{ESA}n] \times [1 - \exp(-b \times TD)]/b/V_{ESA}/TT \tag{8b}$$

wherein $MC_{ESA}$ denotes said mean concentration of the erythropoiesis-stimulating agent, $D_{ESA}$ denotes the dose of the erythropoiesis-stimulating agent and the FIGS. 1, 2, . . . n) following $D_{ESA}$ denote the order of the administration of the erythropoiesis-stimulating agent, b denotes a constant depending on the kind of the erythropoiesis-stimulating agent, TD denotes an interval of the administration of the erythropoiesis-stimulating agent, $V_{ESA}$ denotes a volume of distribution of the erythropoiesis-stimulating agent and TT denotes the number of days between the two points of time.

\* \* \* \* \*